United States Patent
Yatsuzuka et al.

(10) Patent No.: US 7,599,801 B2
(45) Date of Patent: Oct. 6, 2009

(54) PROFILE DATABASE AND METHOD FOR PREPARING PROFILE

(75) Inventors: Shigeru Yatsuzuka, Kanagawa (JP); Isamu Muto, Kanagawa (JP); Iwao Yamashita, Kanagawa (JP); Takuro Tamura, Kanagawa (JP)

(73) Assignee: Hitachi Software Engineering Co., Ltd., Kanagawa (JP)

( * ) Notice: Subject to any disclaimer, the term of this patent is extended or adjusted under 35 U.S.C. 154(b) by 58 days.

(21) Appl. No.: 10/155,631

(22) Filed: May 23, 2002

(65) Prior Publication Data

US 2002/0184201 A1    Dec. 5, 2002

(30) Foreign Application Priority Data

Jun. 4, 2001    (JP) .............................. 2001-168230

(51) Int. Cl.
*G06F 19/00* (2006.01)
(52) U.S. Cl. .......................................... 702/20; 702/19
(58) Field of Classification Search ................... 702/19, 702/20
See application file for complete search history.

(56) References Cited

U.S. PATENT DOCUMENTS

2003/0187587 A1* 10/2003 Swindells et al. ............. 702/19

FOREIGN PATENT DOCUMENTS

| JP | 2002-536710 | 1/2000 |
|---|---|---|
| WO | WO 00/43939 | 1/2000 |

OTHER PUBLICATIONS

Higgins et al. (Methods in Enzymology (1996) vol. 266, pp. 383-402).*

Desmond G. Higgins, et al., "Clustal V: Improved Software for Multiple Sequence Alignment". Cabios, vol. 8, No. 2, (1992), pp. 189-191.

"Introduction to Making and Using Protein Multiple Alignments", (Tutorial notes, Match 1999), http://bioinformatics.weizmann.ac.il/~pietro/Making_and_using_protein_MA/, 7 pages.

Julie D. Thompson et al., "Clustal W: Improving the Sensitivity of Progressive Multiple Sequence alignment Through Sequence Weighting, Position-Specific Gap Penalties and Weight Matrix Choice", Nucleic Acids Research, 1994, vol. 22, No. 22, pp. 4673-4680.

* cited by examiner

*Primary Examiner*—Lori A Clow
(74) *Attorney, Agent, or Firm*—Stites & Harbison PLLC; Juan Carlos A. Marquez, Esq.

(57) ABSTRACT

Provided is a means capable of high-speed analysis of a large-scale correlation among sequences of biopolymers and reutilization of any analyzed profile. A large-scale profile database 103 is provided with which the correlation among sequences of biopolymers can be analyzed at a high speed, and any profile can be extracted from the profile database.

6 Claims, 13 Drawing Sheets

| prf_id | name | profile |
|---|---|---|
| 0000 | Prof 1 | CONDENSED PROFILE |
| 0001 | Prof 2 | ............... |

PROFILE TABLE

| prf_id | seq_id |
|---|---|
| 0000 | 0000 |
| 0000 | 0001 |
| ............ | .......... |
| 0001 | 0001 |
| ............ | .......... |

SEQUENCE MEMBER TABLE

| prf_id | cnd_name | value |
|---|---|---|
| 0000 | method | clustalW V1.8 |
| 0001 | method | clustalW V1.8 |

PROFILE ANALYSIS CONDITION TABLE

| seq_id | seq_name | sequence |
|---|---|---|
| 0000 | U33203 | ACCTG... |
| 0001 | U54801 | ACCTC... |
| ......... | ...... | ...... |

SEQUENCE TABLE

FIG.9

| seq_id \ prof_id | prof 1 | prof 2 | prof 3 | prof 4 | prof 5 | prof 6 | prof 7 | prof 8 |
|---|---|---|---|---|---|---|---|---|
| seq1 | ○ |  |  |  | ○ |  |  | ○ |
| seq2 |  | ○ |  |  | ○ | ○ |  |  |
| seq3 |  |  |  |  | ○ | ○ | ○ |  |
| seq4 |  |  | ○ | ○ |  |  |  | ○ |
| hit# | 1 | 1 | 1 | 1 | 3 | 2 | 1 | 2 |

PROFILE DATABASE AND METHOD FOR PREPARING PROFILE

BACKGROUND OF THE INVENTION

1. Field of the Invention

The present invention relates to a method for preparing a computed profile database in which a correlation among sequences of a plurality of biopolymers is analyzed and the results thereof are accumulated therein, and a method for preparing a correlation diagram or a multiple alignment of sequences at a high speed utilizing the profile database.

2. Prior Art

A conventional method for analyzing the correlation among sequences includes ClustalW (1994-), which is a program prepared by J. Thompson and T. Gibson. A computational method used therein is described in ClustalW (Thompson J. D., Higgins D. G., Gibson T. J., Nucleic Acid Res. 1994, November: 4673-80). Use of ClustalW enables analysis of the correlation of evolutionary systems among different sequences and the preparation of multiple alignments thereof.

The conventional technique, however, has the following drawbacks.

1. In general, an enormously long computation time is necessary in the analysis of the correlation among a large number of sequences. For example, when analysis is performed on 500 nucleic acid sequences having an average sequence length of 1,500 bp using ClustalW, the computation may take about 30 hours. Nowadays, since the sequences of biopolymers such as nucleic acids and amino acids (hereinafter simply referred to as "sequence") are easily decoded and sequence data is mass-produced, such time-consuming analysis of the sequences represents a bottleneck in the advancement of research (a computation time drawback).
2. As the size and number of sequences to be computed increase, in addition to the computation time, the necessary amount of computer memory space is also increased and the computer specifications necessary to complete the computation within a realistic time also become large. However, there are few academic research environments in which such a computer can be used (a computation scale drawback).
3. Although a large amount of computing resources and research time are consumed in individual computations, the reutilization of computation results is not considered (a computation results reutilization drawback).

The object of the present invention is to provide a means for solving the drawbacks of the conventional technique.

SUMMARY OF THE INVENTION

In order to attain the above object, the present invention provides a database having a "profile" as information of the results of analysis of the correlation among sequences accumulated therein in a reutilizable manner. The present invention also provides a novel system for analyzing the correlation among sequences at a high speed through the utilization of profiles accumulated in the profile database. More specifically, when a group of sequences that is the target of analysis of the user is a partial group of sequences constituting a profile entry registered in the profile database, only the information on the results of analysis associated with the target sequences is extracted from the profile entry to be provided to the user as a novel profile. The present invention also provides a method wherein, even when there is no profile entry containing all the target sequences, if there is a profile entry containing a majority of the target sequences, from that profile entry only the information on the results of analysis associated with the target sequences is extracted. Then using the extracted information as an initial profile, analysis is carried out by a method whereby the sequences not contained in the profile entry are added to the initial profile, thereby obtaining the target profile. Thus, in all cases, the computation time can be significantly shortened.

The profile database of the present invention accumulates therein: a profile table storing a profile of results of analysis on multiple alignment and/or a evolutionary system of a plurality of sequences of biopolymers in which an ID, a name, and profile data of each profile are associated with each other or one another; a profile analysis condition table storing an ID of each profile in association with the profile analysis condition of each profile; a sequence member table storing an ID of a profile in association with the sequence ID; and a sequence table storing a sequence ID, sequence name, and sequence of each sequence in association with each other or one another.

The method for preparing the profile for preparation of multiple alignment and/or evolutionary system analysis of a plurality of sequences of biopolymers according to the present invention comprises steps of: inputting a plurality of sequences to be subject to profile preparation; searching the profile database accumulating, as the profile for each group of sequences, the results of analysis on multiple alignment or an evolutionary system for a plurality of groups of sequences, to search for the profile for the group of sequences containing the highest number of input sequences; and performing multiple alignment preparation and/or evolutionary system analysis for the logical sum of the input plurality of sequences and the group of sequences targeted by the searched profile.

At this time, the further provision of a step of registering the results of multiple alignment preparation and/or evolutionary system analysis for the logical sum of the input plurality of sequences and the group of sequences targeted by the searched profile as a novel profile in the profile database is preferred.

BRIEF DESCRIPTION OF THE DRAWINGS

FIG. 4 is a diagram showing an example of multiple alignment.

FIG. 7 is a diagram showing examples of data in the profile database.

FIG. 9 is an explanatory diagram showing the determination of target profile.

EMBODIMENT FOR CARRYING OUT THE INVENTION

An embodiment for carrying out the present invention will be hereinafter described in detail with reference to the accompanying drawings.

Figure 1:
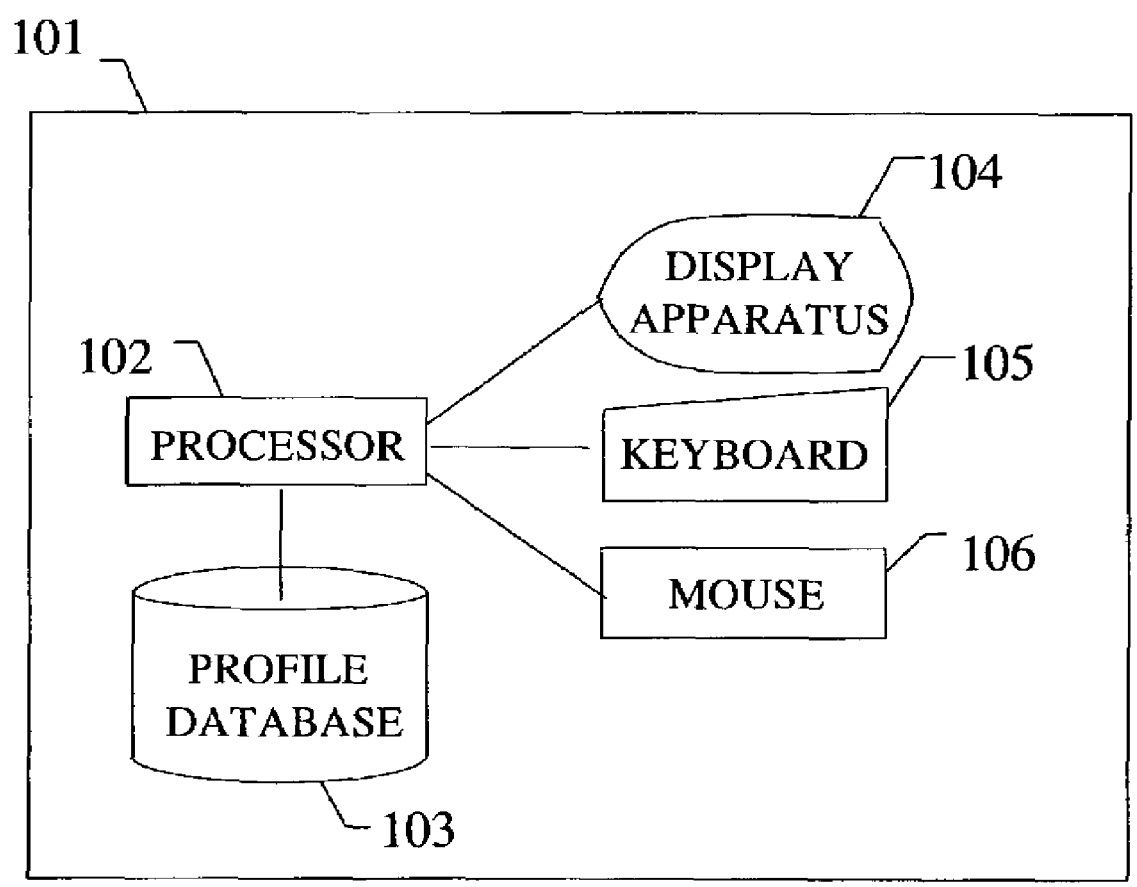
FIG. 1 is a block diagram showing a constitutional example of a system (stand-alone mode) for using a profile database of the present invention.

FIG. 1 is a block diagram showing a constitutional example of a system (stand-alone mode) for using a profile database of the present invention. This system (stand-alone mode) 101 for using a profile database comprises a processor 102, a profile database 103, a display apparatus 104, a keyboard 105, and a mouse 106.

The user inputs sequences of any biopolymers, such as nucleic acids, into processor 102 using keyboard 105 or mouse 106. Processor 102 analyzes the correlation among sequences using the input sequences and profile database 103 and, based on the results, draws a correlation diagram or multiple alignment of sequences on display apparatus 104.

The user also requests processor 102 to display a profile compatible with any condition from profiles in profile database 103 using keyboard 105 or mouse 106. Processor 102, upon reception of the request by the user, accesses profile database 103 and, from all the profiles therein, searches for profiles compatible with the condition input by the user to display a list thereof on display apparatus 104. The user selects any profile from the displayed profiles and requests its display. Processor 102, upon reception of the request by the user, accesses profile database 103 and obtains the requested profile in order to display it on display apparatus 104.

Figure 2:
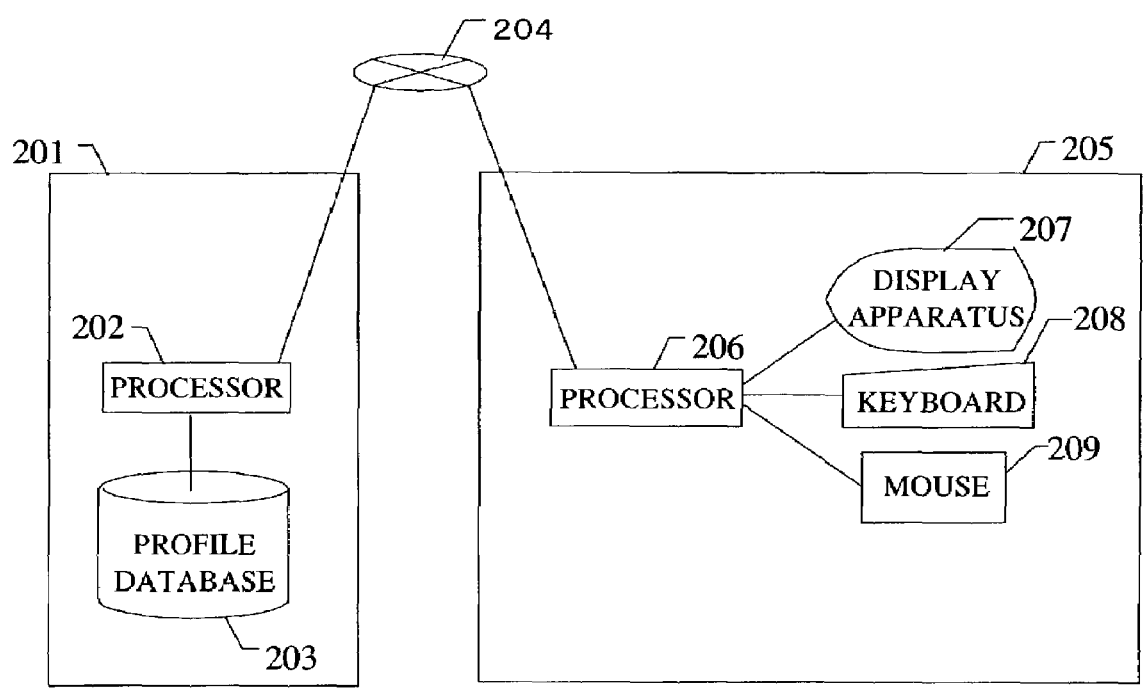
FIG. 2 is a block diagram showing a constitutional example of a system (client-server mode) for using a profile database of the present invention.

FIG. 2 is a block diagram showing a constitutional example of a system (client-server mode) for using a profile database of the present invention. This system (client-server mode) for using a profile database, as shown in FIG. 2, is constituted by a profile database processor 201, a data input/output processor 205, and a communication circuit 204. Profile database processor 201 is constituted by a processor 202 for performing database processing and a profile database 203. Data input/output processor 205 comprises a processor 206 for data input/output processing, a display apparatus 207, a keyboard 208, and a mouse 209.

The user inputs sequences of any biopolymers, such as a nucleic acids, into data input/output processor 205 using keyboard 208 or mouse 209. Data input/output processor 205 transmits the input sequences to profile database processor 201 through communication circuit 204. Profile database processor 201 analyzes the correlation among sequences using the transmitted sequences and profile database 203 and transmits the results to data input/output processor 205 through communication circuit 204. Based on the transmitted results of analysis, data input/output processor 205 draws a correlation diagram or multiple alignment of sequences on display apparatus 207.

The user requests data input/output processor 205, using keyboard 208 or mouse 209, to display a profile which is compatible with the desired condition from profile database 203. Data input/output processor 205, upon reception of the request from the user, transmits the request to database processor 201 through communication circuit 204. Database processor 201, upon reception of the transmitted request, accesses profile database 203 to search for profiles compatible with the condition input by the user from the profile database and transmits a list of compatible profiles to data input/output processor 205 through communication circuit 204. Upon reception of the transmitted list of profiles, data input/output processor 205 displays it on display apparatus 207. The user selects any profile from the displayed list of profiles and requests data input/output processor 205 to display the profile. Data input/output processor 205 transmits the request from the user to database processor 201 using communication circuit 204. Database processor 201, upon reception of the transmitted request, accesses profile database 203, obtains the requested profile, and transmits it to data input/output processor 205. Data input/output processor 205 displays the transmitted profile on display apparatus 207.

Figure 3:
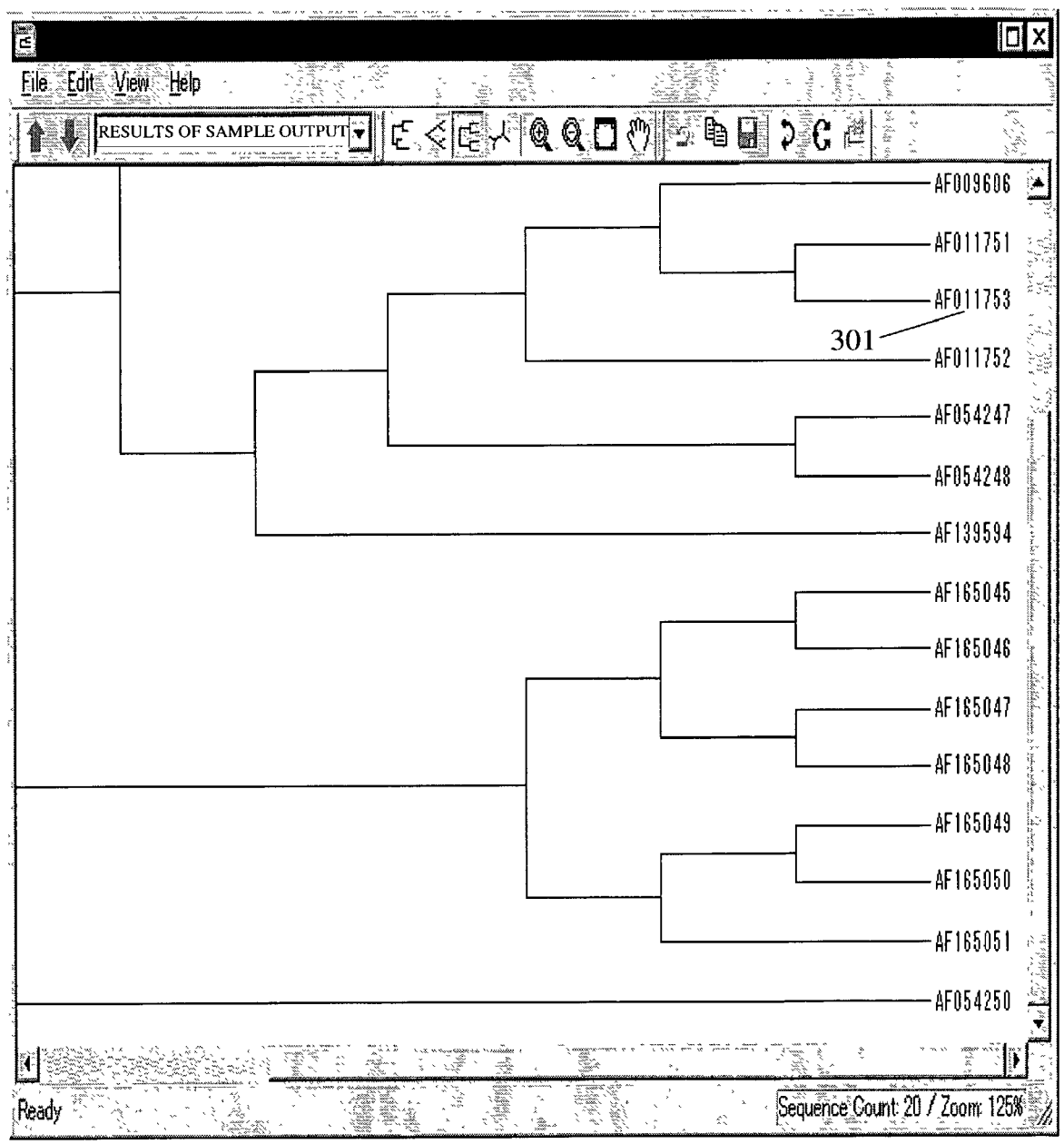
FIG. 3 is a diagram showing an example of a tree diagram.

FIG. 3 is a diagram showing an example of a tree diagram representing the correlation among sequences displayed on display apparatus 104 or display apparatus 207. This diagram shows an evolutionary system among sequences. The character strings at the right side of the tree diagram respectively represent the sequence name of each sequence.

Figure 4:
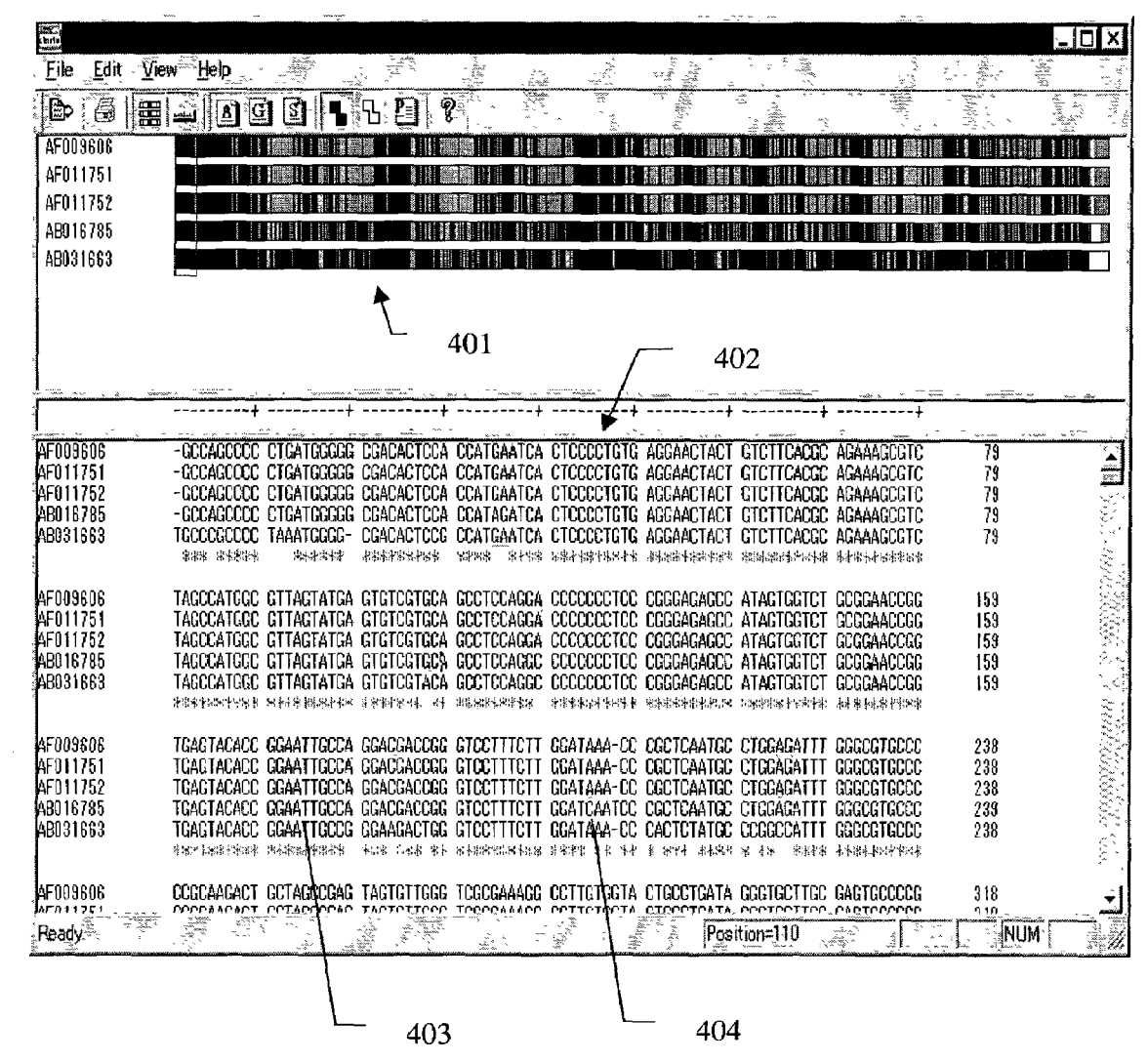

FIG. 4 is a diagram showing an example of a multiple alignment of sequences (a display system in which a plurality of sequences are aligned and agreement/disagreement among the sequences is clearly displayed) displayed on display apparatus 104 or display apparatus 207. The upper part of the screen is a schematic diagram 401 representing the multiple alignments, which displays the total length of an alignment sequence. The lower part of the screen shows an alignment sequence 402. In alignment sequence 402, a portion 403 in which all the sequences SEQ IDs 1-16 are matching can be separated by color from a portion 404 in which the frequency of agreement among sequences is at a certain level or more.

Figure 5:
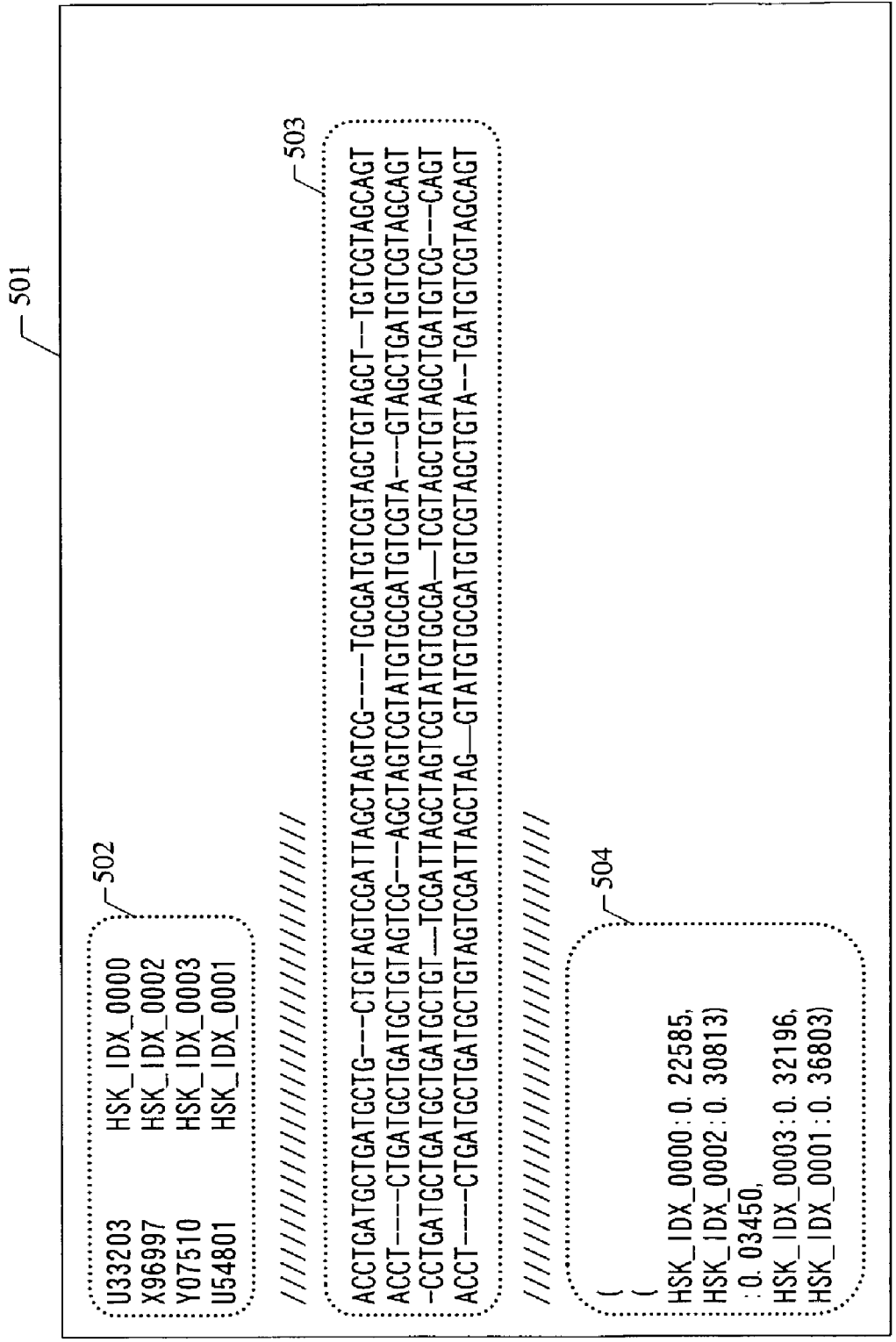
FIG. 5 is a diagram showing an example of profile data.

SEQ ID 1: gccagccccc tgatgggggc gacactccac catgaatcac tcccctgtga ggaactactg tcttcacgca gaaagcgtc SEQ ID 2: gccagccccc tgatgggggc gacactccac catgaatcac tcccctgtga ggaactactg tcttcacgca gaaagcgtc SEQ ID 3: gccagccccc tgatgggggc gacactccac catgaatcac tcccctgtga ggaactactg tcttcacgca gaaagcgtc SEQ ID 4: gccagccccc tgatgggggc gacactccac catagatcac tcccctgtga ggaactactg tcttcacgca gaaagcgtc SEQ ID 5: tgcccgcccc taaatggggc gacactccgc catgaatcac tcccctgtga ggaactactg tcttcacgca gaaagcgtc SEQ ID 6: tagccatggc gttagtatga gtgtcgtgca gcctccagga cccccctcc cgggagagcc atagtggtct gcggaaccgg SEQ ID 7: tagccatggc gttagtatga gtgtcgtgca gcctccagga cccccctcc cgggagagcc atagtggtct gcggaaccgg SEQ ID 8: tagccatggc gttagtatga gtgtcgtgca gcctccagga cccccctcc cgggagagcc atagtggtct gcggaaccgg SEQ ID 9: tagccatggc gttagtatga gtgtcgtgca gcctccaggc cccccctcc cgggagagcc atagtggtct gcggaaccgg SEQ ID 10: tagccatggc gttagtatga gtgtcgtaca gcctccaggc cccccctcc cgggagagcc atagtggtct gcggaaccgg SEQ ID 11: tgagtacacc ggaattgcca ggacgaccgg gtcctttctt ggataaaccc gctcaatgcc tggagatttg ggcgtgccc SEQ ID 12: tgagtacacc ggaattgcca ggacgaccgg gtcctttctt ggataaaccc gctcaatgcc tggagatttg ggcgtgccc SEQ ID 13: tgagtacacc ggaattgcca ggacgaccgg gtcctttctt ggataaaccc gctcaatgcc tggagatttg ggcgtgccc SEQ ID 14: tgagtacacc ggaattgcca ggacgaccgg gtcctttctt ggatcaatcc cgctcaatgc ctggagattt gggcgtgccc SEQ ID 15: tgagtacacc ggaattgccg ggaagactgg gtcctttctt ggataaaccc actctatgcc cggccatttg ggcgtgccc SEQ ID 16: ccgcaagact gctagccgag tagtgttggg tcgcgaaagg ccttgtggta ctgcctgata gggtgcttgc gagtgccccg FIG. 5 is a diagram showing an example of profile data. This format is for the case where ClustalW was used in the computation for analyzing the correlation among sequences. One profile 501 comprises an item 502 (sequence name and sequence ID), an item 503 (alignment sequence), and an item 504 (results of analysis on the correlation among sequences). Item 502 is the sequence names and sequence IDs contained in the profile. Item 503 displays each sequence in the profile (SEQ IDs 17-30) in the form of a multiple alignment. The sequences must be aligned in the same order as in item 502. Item 504 is a result of analysis on the correlation among sequences in the profile. The numerical value at the right side of each sequence ID represents the distance between an individual sequence and a sequence upstream of it in the evolutionary system. The larger this distance, the more disagreement between two sequences from the viewpoint of the evolutionary system.

Figure 6:
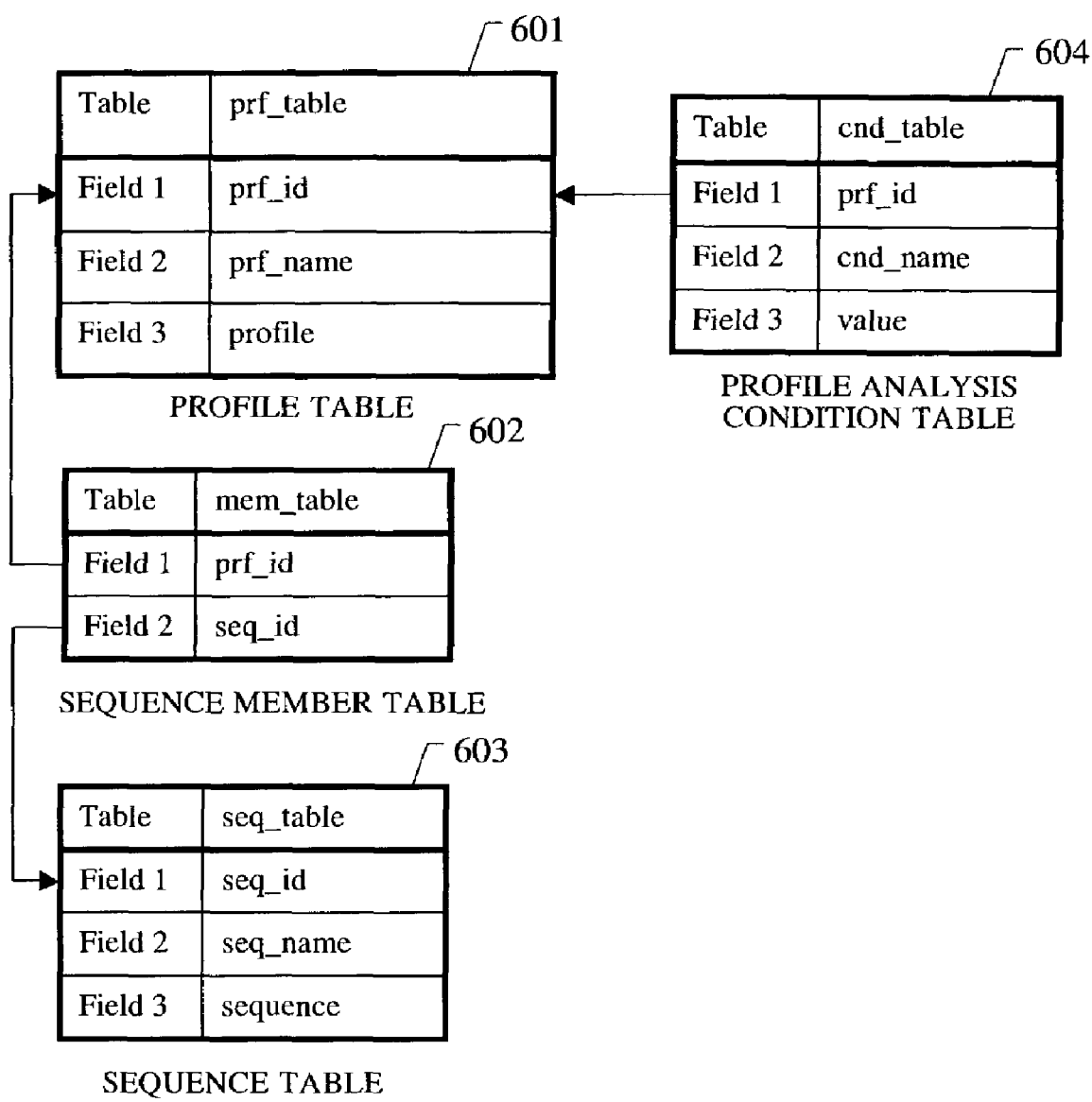
FIG. 6 is a diagram showing a definition of tables used in the profile database.

SEQ ID 17: acctgatgctgatgctg
SEQ ID 18: ctgtagtcgattagctagtcg
SEQ ID 19: tgcgatgtcgtagctgtagct
SEQ ID 20: tgtcgtagcagtacct
SEQ ID 21: ctgatgctgatgctgtagtcg
SEQ ID 22: agctagtcgtatgtgcgcgatgtcgta
SEQ ID 23: gtagctgatgtcgtagcagt
SEQ ID 24: cctgatgctgatgctgatgctgt
SEQ ID 25: tcgattagctagtcgtatgtgcga
SEQ ID 26: tcgtagctgtagctgatgtcg
SEQ ID 27: cagtacct
SEQ ID 28: ctgatgctgatgctgtagtcgattagctag
SEQ ID 29: gtatgtgcgatgtcgtagctgta
SEQ ID 30: tgatgtcgtagcagt FIG. 6 is a diagram showing a definition of tables used in the profile database. A profile table 601 stores the ID (prf_id), name (prf_name) and profile (profile) of each profile in the profile database. Each profile is condensed and, thus, can be compactly stored in the profile database.

A sequence member table 602 stores a profile ID (prf_id) and each sequence ID (seq_id). Each sequence ID in this table should be present in a sequence table 603, and each profile ID in this table should be present in profile table 601. In this table, one profile ID has a plurality of sequence IDs, and, conversely, one sequence ID has a plurality of profile IDs. Use of this table enables high-speed searching for the optimal profile for use in the preparation of a correlation diagram or multiple alignment of sequences without the necessity of accessing individual profiles.

Sequence table 603 stores each sequence (sequence), sequence name (seq_name), and sequence ID (seq_id) that is in the profile database. A profile analysis condition table 604 stores the ID of each profile (prf_id), an analysis condition name (cnd_name), and a condition value (value). Each profile ID in this table should be present in table 601.

FIG. 7 is a diagram showing examples of data in the profile database. The sequence member table shows that one profile ID has a plurality of sequence IDs, and, conversely, one sequence ID has a plurality of profile IDs. This is because one profile contains a plurality of sequences, while different profiles sometimes contain the same sequence.

Figure 8:
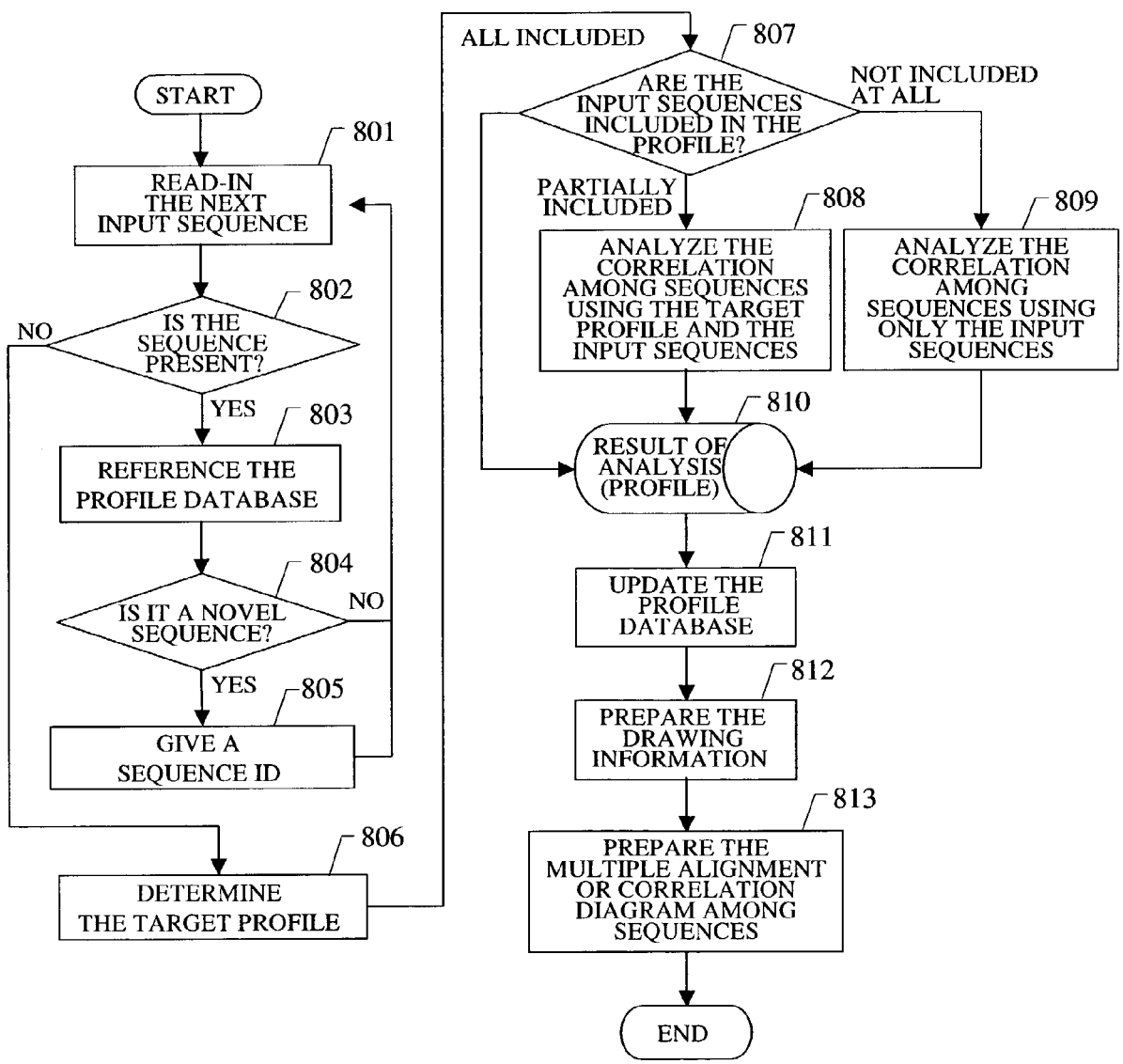
FIG. 8 is a flow chart describing a process for preparing a correlation diagram or multiple alignment.

FIG. 8 is a flow chart explaining in detail a process for preparing a correlation diagram or multiple alignment of sequences in the systems for using the profile database that are described in FIGS. 1 and 2. ClustalW is used in the analysis on the correlation among sequences.

Upon initiation of processing, sequences such as input nucleic acid sequences are read-in (801). The presence of the read-in sequence is judged (802), and if the sequence is present, it is referenced with the profile database (803), and whether the input sequence is novel (not present in the profile database) or not is judged (804). When there is a sequence in the profile database that is completely matching with the input sequence, the input sequence is determined as an "existing sequence." In all other cases, the input sequence is determined as a "novel sequence." When the input sequence is novel, the sequence is given a sequence ID (805). After all the sequences are read-in, the target profile to be used in the multiple alignment or evolutionary system analysis computation is determined (806).

Once the target profile is determined, whether or not the profile includes the input sequences is judged (807). When all the input sequences are included in the target profile, the target profile, as it is, is taken as a result of analysis 810 without analyzing the correlation among sequences. When a part of the input file is included in the target profile, the correlation among sequences is analyzed by ClustalW using the target profile and the input sequences (808), to output result of analysis 810. When the target profile includes none of the input sequences, only the input sequences are used to analyze the correlation among sequences by ClustalW (809), to output result of analysis 810. Once the result of analysis is output, the profile database is updated using result of analysis 810 (811). Then, information for drawing the correlation diagram or multiple alignment of sequences is prepared (812) and the correlation diagram or multiple alignment of sequences is drawn on the display apparatus (813).

Figure 9:
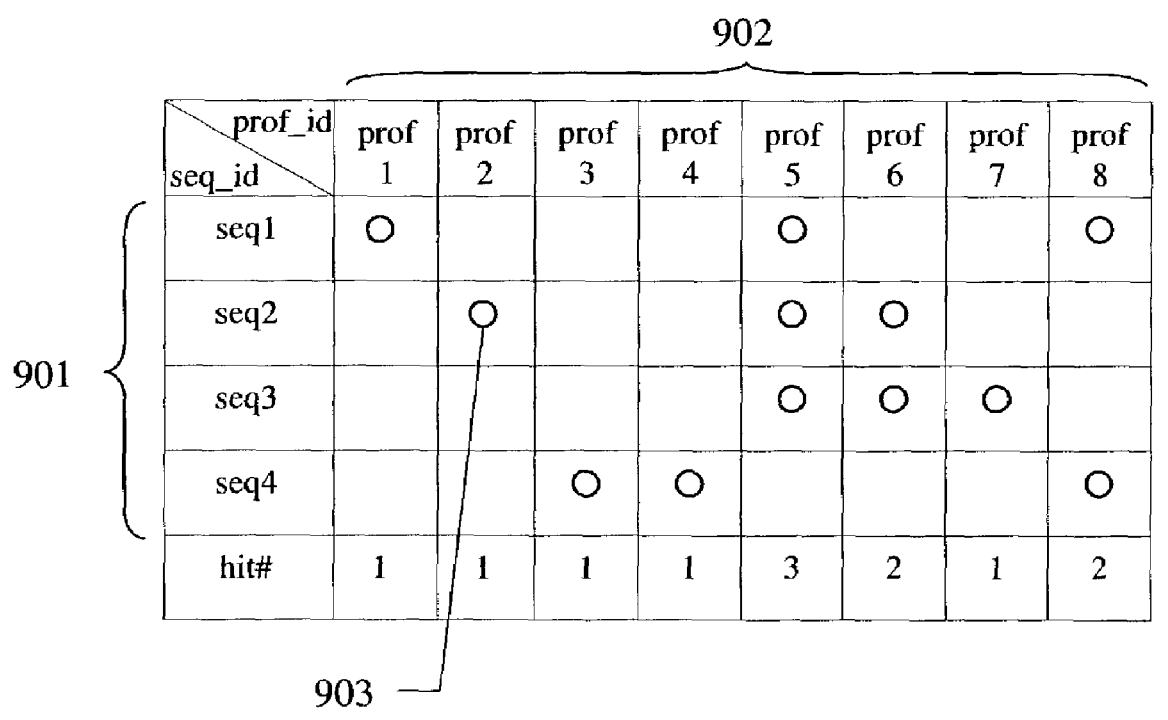

FIG. 9 is an explanatory view on the method for determining the target profile for the input sequences in FIG. 8. As shown in FIG. 9, a chart is created in which a vertical axis 901 represents input sequences and a horizontal axis 902 represents profiles in the database. For example, if seq2, which is one of the input sequences seq1, seq2, . . . , is included in prof2, which is one of the profiles in the database, i.e., one of prof1, prof2, . . . , a mark 903 is provided at the position where seq2 intersects with prof2. This operation is carried out for all the input sequences and the number of marks (hits) is recorded for each profile. As a result, the profile having the highest number of "hits" is determined as the target profile. In the case of the example in FIG. 9, prof5 would be determined as the target profile.

When there are a plurality of profiles having the highest number of "hits," a method exists whereby, of the candidate profiles, the profile having the highest ratio of the number of input sequences with respect to the number of sequences included in each profile is determined as the target profile (effective in the preparation of a small-scale correlation diagram or multiple aliginment), and a method exists whereby, of the candidate profiles, the profile having the lowest ratio of the number of input sequences with respect to the number of sequences included in each profile is determined as the target profile (effective in the preparation of a large-scale correlation diagram or multiple alignment). For example, when the "hits" of prof4 and prof5 are both "3" and this is the highest number among all the profiles, and the number of sequences included in prof4 is "6" and the number of sequences included in prof5 is "30," in the former method, the target profile is prof4 and, in the latter method, it is prof5.

Figure 10:
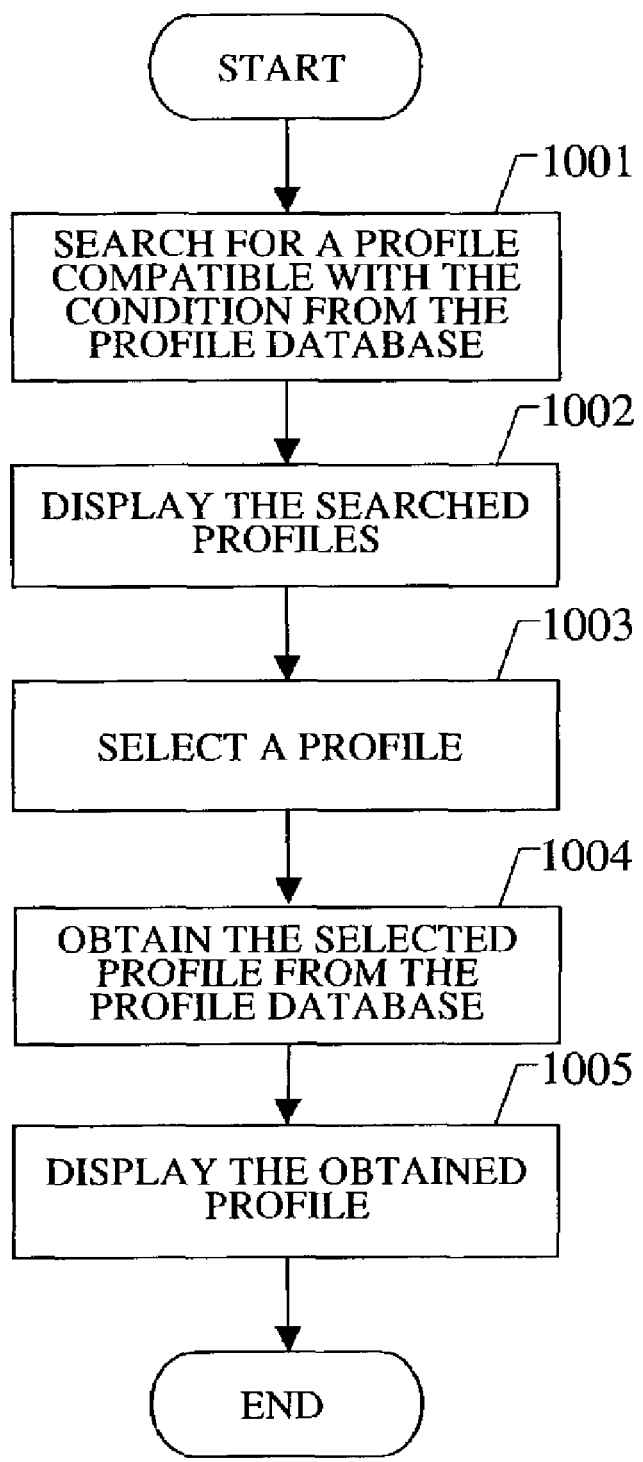
FIG. 10 is a flow chart describing display processing of profile data.

FIG. 10 is a flow chart describing in detail the process for displaying any profile data in the systems for using the profile database as described in FIGS. 1 and 2. Upon initiation of processing, the program searches for a profile compatible with the condition input by the user from the profile database (1001) and displays compatible profiles on a display apparatus (1002). The user selects any profile from the displayed profiles (1003). The program obtains the selected profile from the profile database (1004) and displays it on a display apparatus (1005).

Figure 11:
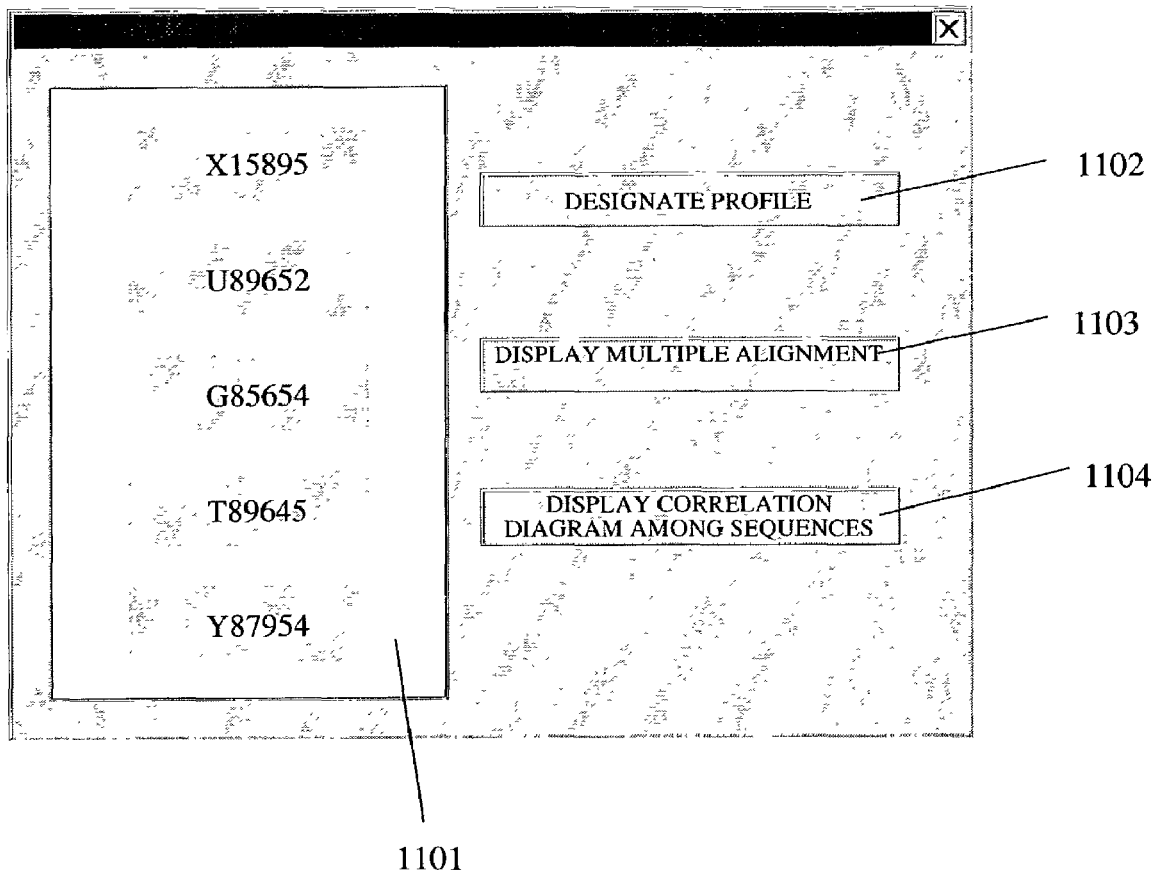
FIG. 11 is a diagram showing an example of a user interface (main dialog) for inputting a sequence.
Figure 12:
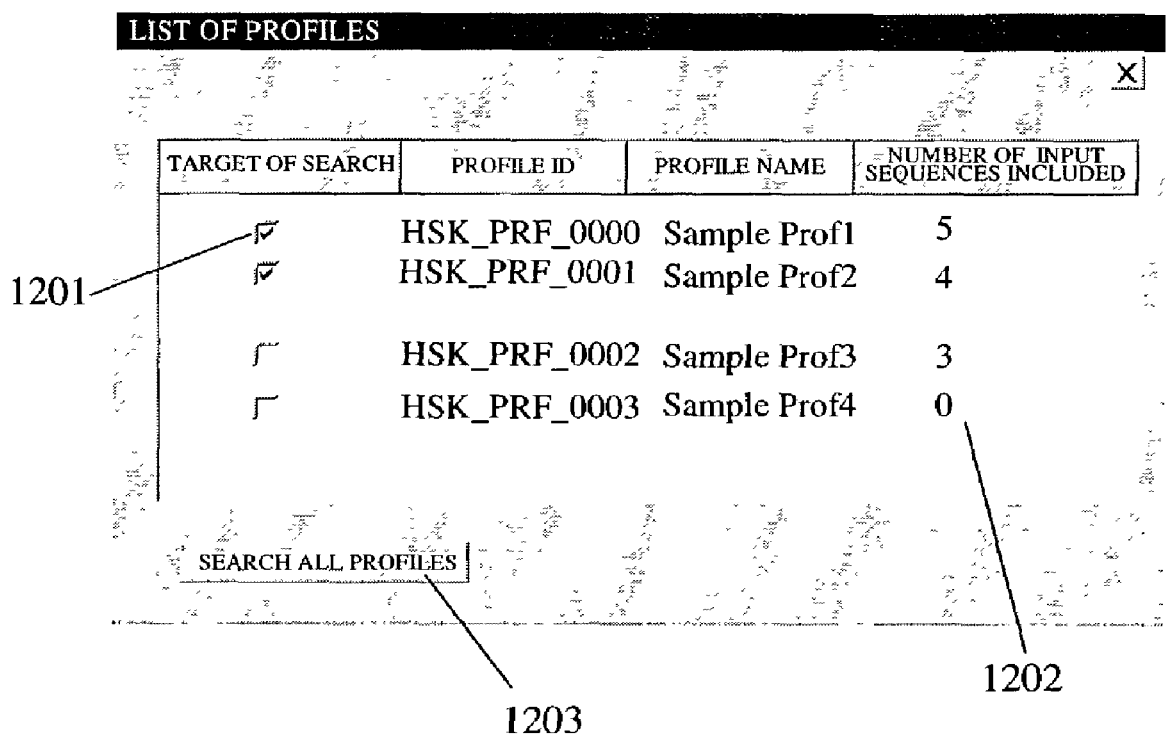
FIG. 12 is a diagram showing an example of a user interface (profile dialog) for inputting a sequence.

FIG. 11 is a diagram showing an example of a main dialog among the user interfaces for inputting sequences for the preparation of a correlation diagram or multiple alignment of sequences in the systems for using the profile database described in FIGS. 1 and 2. In a main dialog (FIG. 11), the user first drags and drops sequence files, such as those of nucleic acid sequences, to input in a file window 1101. Next, the user presses a "DESIGNATE PROFILE" button 1102 to start a profile dialog (FIG. 12). When the profile dialog is started, a list of all the profiles in the profile database is displayed in order of the number of input sequences included, from highest to lowest, with the profile containing the highest number of the input sequences at the top. The number of input sequences included in each profile is computed when the dialog is started and displayed in a "NUMBER OF INPUT SEQUENCES INCLUDED" column 1202. The user can check a target of search column 1201 for each profile to designate a profile to be used in the analysis on the correlation among sequences. When all the profiles in the profile database are to be used, a "SEARCH ALL PROFILES" button 1203 is pressed.

Upon completion of designation of the profiles, the user returns to the main dialog (FIG. 11) and presses a "DISPLAY THE MULTIPLE ALIGNMENT" button 1103 to display a multiple alignment (FIG. 4) or presses a "DISPLAY THE CORRELATION DIAGRAM AMONG SEQUENCES" button 1104 to display a tree diagram (FIG. 3) representing the correlation among sequences. When a profile was not designated, a suitable target profile is determined in the manner described in FIG. 8 to display the multiple alignment or the tree diagram.

Figure 13:
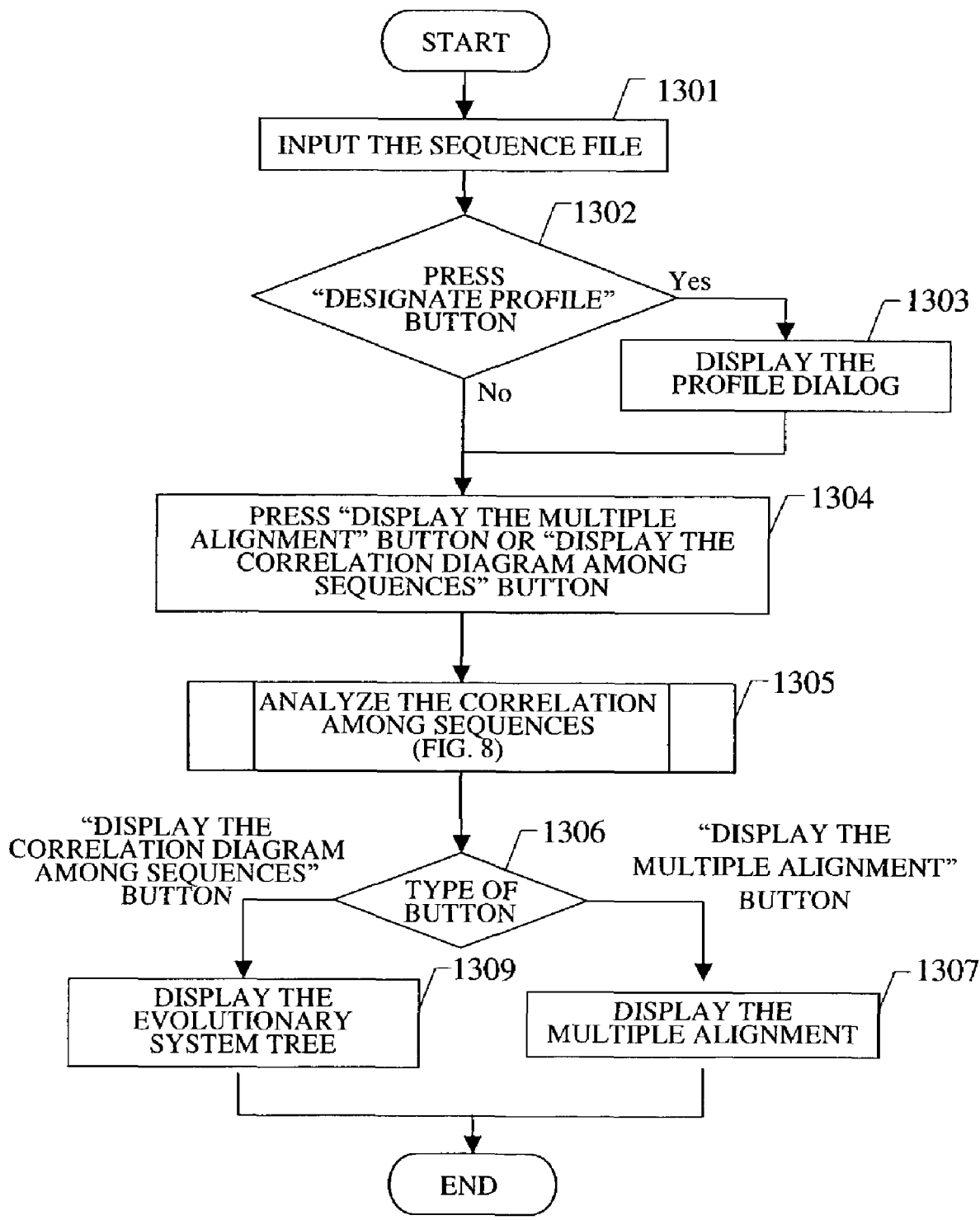
FIG. 13 is a diagram showing a procedure for using a user interface for inputting a sequence.

FIG. 13 is an explanatory view on the process for using the user interface for inputting sequences for the preparation of a correlation diagram or multiple alignment of sequences in the system for using a profile database as described in FIGS. 11 and 12.

Upon initiation of processing, the input of sequence files by means of drag and drop by the user is accepted (1301). When the "DESIGNATE PROFILE" button is pressed (1302) after the input of files is completed, a profile dialog is displayed (1303). Thereafter, when the "DISPLAY THE MULTIPLE ALIGNMENT" button or the "DISPLAY THE CORRELATION DIAGRAM AMONG SEQUENCES" button is pressed (1304), the designated profiles are used to analyze the correlation among sequences (1305). Upon completion of the analysis, the type of button pressed by the user is determined (1306). If the "DISPLAY THE MULTIPLE ALIGNMENT" button was pressed, a multiple alignment is displayed (1307), and if the "DISPLAY THE CORRELATION DIAGRAM AMONG SEQUENCES" button was pressed, an evolutionary system tree is displayed.

Effect of the Invention

As is apparent from the foregoing description, the present invention can provide a means for obtaining, at a high speed, results of analysis on the correlation among sequences, which has hitherto been extremely time consuming, using analyzed data accumulated in a profile database.

What is claimed is:

1. A computer-implemented method for preparing a profile of sequences of biological polymers, comprising:

obtaining by a suitably programmed computer access to a profile database having profiles registered therein in advance, each of the profiles being obtained by at least one of multiple alignment analysis and evolutionary relationship analysis among a group of sequences of biological polymers, each profile including sequence names of sequences contained in the group, corresponding sequence IDs of sequences contained in the group, and a correlation diagram or multiple alignments obtained by performing said at least one of multiple alignment analysis and evolutionary relationship analysis on the group;

receiving by the computer a plurality of sequences of interest for which a new profile is to be prepared;

searching by the computer the profile database for a target profile of a sequence group that contains the largest number of sequences included in the plurality of sequences of interest;

determining by the computer if each of the plurality of sequences of interest is included in the target profile thereby deciding if it is necessary to perform at least one of multiple alignment analysis and evolutionary relationship analysis on some or all of the plurality of sequences of interest based on a correlation diagram or multiple alignments contained in the target profile;

performing by the computer said at least one of multiple alignment analysis and evolutionary relationship analysis on either only some or none of the plurality of sequences of interest based on a correlation diagram or multiple alignments contained in the target profile without performing said at least one of multiple alignment analysis and evolutionary relationship analysis among the sequence group of the target profile again;

incorporating by the computer names of the sequences of interest, corresponding sequence IDs, and a correlation diagram or multiple alignments obtained by the performing step into the target profile as the new profile;

registering by the computer the new profile in the profile database; and displaying by a display apparatus a correlation diagram or multiple alignments of the sequences of interest contained in the new profile, wherein when each of the plurality of sequences of interest is included in the target profile, the target profile is determined by the computer as the new profile without performing said at least one of multiple alignment analysis and evolutionary relationship analysis on the plurality of sequences of interest, and wherein when the plurality of sequences of interest are partially included in the target profile, said at least one of multiple alignment analysis and evolutionary relationship is necessarily performed by the computer on sequence of the plurality of sequences of interest which are not contained in the sequence group of the target profile, based on said correlation diagram or multiple alignments contained in the target profile, to obtain the new profile.

2. The computer-implemented method for preparing a profile of sequences of biological polymers according to claim 1, wherein said multiple alignment analysis and evolutionary relationship analysis are conducted with ClustalW.

3. The computer-implemented method for preparing a profile of sequences of biological polymers according to claim 1, wherein when only some but not all sequences in the target profile are included in the plurality of sequences of interest, the information on said some but not all sequences in the target profile is extracted to be processed to the new profile.

4. The computer-implemented method for preparing a profile of sequences of biological polymers according to claim 1, wherein when the plurality of sequences of interest are not included in the target profile at all, said at least one of multiple alignment analysis and evolutionary relationship is performed by the computer on all of the plurality of sequences of interest, based on said correlation diagram or multiple alignments contained in the target profile, to obtain the new profile.

5. A computer-implemented method for preparing a profile of sequences of biological polymers by using a profile database having profiles registered therein in advance, each of the profiles being obtained by multiple alignment analysis and evolutionary relationship analysis among a group of sequences of biological polymers, each profile including sequence names of sequences contained in the group, corresponding sequence IDs of sequences contained in the group, multiple alignment analysis result of sequences contained in the group, and evolutionary relationship analysis result of sequences contained in the group, comprising:
- a sequences receiving step of receiving by a suitably programmed computer a plurality of sequences of interest;
- a target profile determining step of determining by the computer a target profile for the plurality of sequences of interest by searching the profile database for the target profile that contains the largest number of sequences included in the plurality of sequences of interest;
- a profile preparing step of preparing by the computer a profile for the plurality of sequences of interest without performing said at least one of multiple alignment analysis and evolutionary relationship analysis among the sequence group of the target profile again, by performing, according to the result of the target profile determining step, one of processes including:
  (1) a step of using by the computer the target profile determined in the target profile determining step as a profile for the plurality of sequences of interests as is, when all of the plurality of sequences of interest is included in the target profile, and
  (2) a step of preparing by the computer the profile for the plurality of sequences of interest by using the target profile and performing multiple alignment analysis and evolutionary relationship analysis only on sequences of the plurality of sequences of interest which are not contained in the target profile, when the plurality of sequences of interest is partially included in the target profile;
- a profile registering step of registering by the computer the profile for the plurality of sequences of interest prepared in the profile preparing step in the profile database; and
- a displaying step of displaying by a display apparatus a correlation diagram of the sequences of interest contained in the profile prepared in the profile preparing step.

6. The computer-implemented method according to claim 5, further comprising a step for preparing by the computer the profile for the plurality of sequences of interest by performing multiple alignment analysis and evolutionary relationship analysis on each of the plurality of sequences of interest, when none of the plurality of sequences of interest is included in any profiles in the profile database.

* * * * *

UNITED STATES PATENT AND TRADEMARK OFFICE
CERTIFICATE OF CORRECTION

PATENT NO.        : 7,599,801 B2
APPLICATION NO.   : 10/155631
DATED             : October 6, 2009
INVENTOR(S)       : Yatsuzuka et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 494 days.

Signed and Sealed this

Twenty-eighth Day of September, 2010

David J. Kappos
*Director of the United States Patent and Trademark Office*

```
                        SEQUENCE LISTING

<160> NUMBER OF SEQ ID NOS: 30

<210> SEQ ID NO 1
<211> LENGTH: 79
<212> TYPE: DNA
<213> ORGANISM: Artificial Sequence
<220> FEATURE:
<223> OTHER INFORMATION: chemically synthesized

<400> SEQUENCE: 1
gccagccccc tgatgggggc gacactccac catgaatcac tccctgtga ggaactactg     60 tcttcacgca gaaagcgtc                                                 79

<210> SEQ ID NO 2
<211> LENGTH: 79
<212> TYPE: DNA
<213> ORGANISM: Artificial Sequence
<220> FEATURE:
<223> OTHER INFORMATION: chemically synthesized

<400> SEQUENCE: 2
gccagccccc tgatgggggc gacactccac catgaatcac tccctgtga ggaactactg     60 tcttcacgca gaaagcgtc                                                 79

<210> SEQ ID NO 3
<211> LENGTH: 79
<212> TYPE: DNA
<213> ORGANISM: Artificial Sequence
<220> FEATURE:
<223> OTHER INFORMATION: chemically synthesized

<400> SEQUENCE: 3
gccagccccc tgatgggggc gacactccac catgaatcac tccctgtga ggaactactg     60 tcttcacgca gaaagcgtc                                                 79
```

<210> SEQ ID NO 4
<211> LENGTH: 79
<212> TYPE: DNA
<213> ORGANISM: Artificial Sequence
<220> FEATURE:
<223> OTHER INFORMATION: chemically synthesized

<400> SEQUENCE: 4
gccagccccc tgatgggggc gacactccac catagatcac tccctgtga ggaactactg      60 tcttcacgca gaaagcgtc                                                 79

<210> SEQ ID NO 5
<211> LENGTH: 79
<212> TYPE: DNA
<213> ORGANISM: Artificial Sequence
<220> FEATURE:
<223> OTHER INFORMATION: chemically synthesized

<400> SEQUENCE: 5
tgcccgcccc taaatggggc gacactccgc catgaatcac tccctgtga ggaactactg      60 tcttcacgca gaaagcgtc                                                 79

<210> SEQ ID NO 6
<211> LENGTH: 80
<212> TYPE: DNA
<213> ORGANISM: Artificial Sequence
<220> FEATURE:
<223> OTHER INFORMATION: chemically synthesized

<400> SEQUENCE: 6
tagccatggc gttagtatga gtgtcgtgca gcctccagga ccccccctcc cgggagagcc      60
atagtggtct gcggaaccgg                                                80

<210> SEQ ID NO 7
<211> LENGTH: 80
<212> TYPE: DNA
<213> ORGANISM: Artificial Sequence
<220> FEATURE:
<223> OTHER INFORMATION: chemically synthesized

<400> SEQUENCE: 7
tagccatggc gttagtatga gtgtcgtgca gcctccagga ccccccctcc cgggagagcc      60
atagtggtct gcggaaccgg                                                80

<210> SEQ ID NO 8
<211> LENGTH: 80
<212> TYPE: DNA
<213> ORGANISM: Artificial Sequence
<220> FEATURE:
<223> OTHER INFORMATION: chemically synthesized

<400> SEQUENCE: 8
tagccatggc gttagtatga gtgtcgtgca gcctccagga ccccccctcc cgggagagcc      60
atagtggtct gcggaaccgg                                                80

<210> SEQ ID NO 9
<211> LENGTH: 80
<212> TYPE: DNA
<213> ORGANISM: Artificial Sequence
<220> FEATURE:
<223> OTHER INFORMATION: chemically synthesized -continued

<400> SEQUENCE: 9
tagccatggc gttagtatga gtgtcgtgca gcctccaggc cccccctcc cgggagagcc    60 atagtggtct gcggaaccgg                                               80

<210> SEQ ID NO 10
<211> LENGTH: 80
<212> TYPE: DNA
<213> ORGANISM: Artificial Sequence
<220> FEATURE:
<223> OTHER INFORMATION: chemically synthesized

<400> SEQUENCE: 10
tagccatggc gttagtatga gtgtcgtaca gcctccaggc cccccctcc cgggagagcc    60 atagtggtct gcggaaccgg                                               80

<210> SEQ ID NO 11
<211> LENGTH: 79
<212> TYPE: DNA
<213> ORGANISM: Artificial Sequence
<220> FEATURE:
<223> OTHER INFORMATION: chemically synthesized

<400> SEQUENCE: 11
tgagtacacc ggaattgcca ggacgaccgg gtcctttctt ggataaaccc gctcaatgcc    60
tggagatttg ggcgtgccc                                                79

<210> SEQ ID NO 12
<211> LENGTH: 79
<212> TYPE: DNA
<213> ORGANISM: Artificial Sequence
<220> FEATURE:
<223> OTHER INFORMATION: chemically synthesized

<400> SEQUENCE: 12
tgagtacacc ggaattgcca ggacgaccgg gtcctttctt ggataaaccc gctcaatgcc    60
tggagatttg ggcgtgccc                                                79

<210> SEQ ID NO 13
<211> LENGTH: 79
<212> TYPE: DNA
<213> ORGANISM: Artificial Sequence
<220> FEATURE:
<223> OTHER INFORMATION: chemically synthesized

<400> SEQUENCE: 13
tgagtacacc ggaattgcca ggacgaccgg gtcctttctt ggataaaccc gctcaatgcc    60
tggagatttg ggcgtgccc                                                79

<210> SEQ ID NO 14
<211> LENGTH: 80
<212> TYPE: DNA
<213> ORGANISM: Artificial Sequence
<220> FEATURE:
<223> OTHER INFORMATION: chemically synthesized

<400> SEQUENCE: 14
tgagtacacc ggaattgcca ggacgaccgg gtcctttctt ggatcaatcc cgctcaatgc    60
ctggagattt gggcgtgccc                                               80

<210> SEQ ID NO 15
<211> LENGTH: 79

```
<212> TYPE: DNA
<213> ORGANISM: Artificial Sequence
<220> FEATURE:
<223> OTHER INFORMATION: chemically synthesized

<400> SEQUENCE: 15
tgagtacacc ggaattgccg ggaagactgg gtcctttctt ggataaaccc actctatgcc      60
cggccatttg ggcgtgccc                                                  79

<210> SEQ ID NO 16
<211> LENGTH: 80
<212> TYPE: DNA
<213> ORGANISM: Artificial Sequence
<220> FEATURE:
<223> OTHER INFORMATION: chemically synthesized

<400> SEQUENCE: 16
ccgcaagact gctagccgag tagtgttggg tcgcgaaagg ccttgtggta ctgcctgata      60
gggtgcttgc gagtgccccg                                                 80

<210> SEQ ID NO 17
<211> LENGTH: 17
<212> TYPE: DNA
<213> ORGANISM: Artificial Sequence
<220> FEATURE:
<223> OTHER INFORMATION: chemically synthesized

<400> SEQUENCE: 17
acctgatgct gatgctg                                                    17

<210> SEQ ID NO 18
<211> LENGTH: 21
<212> TYPE: DNA
<213> ORGANISM: Artificial Sequence
<220> FEATURE:
<223> OTHER INFORMATION: chemically synthesized

<400> SEQUENCE: 18
ctgtagtcga ttagctagtc g                                               21

<210> SEQ ID NO 19
<211> LENGTH: 21
<212> TYPE: DNA
<213> ORGANISM: Artificial Sequence
<220> FEATURE:
<223> OTHER INFORMATION: chemically synthesized

<400> SEQUENCE: 19
tgcgatgtcg tagctgtagc t                                               21

<210> SEQ ID NO 20
<211> LENGTH: 16
<212> TYPE: DNA
<213> ORGANISM: Artificial Sequence
<220> FEATURE:
<223> OTHER INFORMATION: chemically synthesized

<400> SEQUENCE: 20
tgtcgtagca gtacct                                                     16

<210> SEQ ID NO 21
<211> LENGTH: 21
<212> TYPE: DNA
<213> ORGANISM: Artificial Sequence
<220> FEATURE:
```

```
<223> OTHER INFORMATION: chemically synthesized

<400> SEQUENCE: 21
ctgatgctga tgctgtagtc g                                                  21

<210> SEQ ID NO 22
<211> LENGTH: 25
<212> TYPE: DNA
<213> ORGANISM: Artificial Sequence
<220> FEATURE:
<223> OTHER INFORMATION: chemically synthesized

<400> SEQUENCE: 22
agctagtcgt atgtgcgatg tcgta                                              25

<210> SEQ ID NO 23
<211> LENGTH: 20
<212> TYPE: DNA
<213> ORGANISM: Artificial Sequence
<220> FEATURE:
<223> OTHER INFORMATION: chemically synthesized

<400> SEQUENCE: 23
gtagctgatg tcgtagcagt                                                    20

<210> SEQ ID NO 24
<211> LENGTH: 23
<212> TYPE: DNA
<213> ORGANISM: Artificial Sequence
<220> FEATURE:
<223> OTHER INFORMATION: chemically synthesized

<400> SEQUENCE: 24
cctgatgctg atgctgatgc tgt                                                23

<210> SEQ ID NO 25
<211> LENGTH: 24
<212> TYPE: DNA
<213> ORGANISM: Artificial Sequence
<220> FEATURE:
<223> OTHER INFORMATION: chemically synthesized

<400> SEQUENCE: 25
tcgattagct agtcgtatgt gcga                                               24

<210> SEQ ID NO 26
<211> LENGTH: 21
<212> TYPE: DNA
<213> ORGANISM: Artificial Sequence
<220> FEATURE:
<223> OTHER INFORMATION: chemically synthesized

<400> SEQUENCE: 26
tcgtagctgt agctgatgtc g                                                  21

<210> SEQ ID NO 27
<211> LENGTH: 8
<212> TYPE: DNA
<213> ORGANISM: Artificial Sequence
<220> FEATURE:
<223> OTHER INFORMATION: chemically synthesized

<400> SEQUENCE: 27 cagtacct                                                                  8
```

```
-continued

<210> SEQ ID NO 28
<211> LENGTH: 30
<212> TYPE: DNA
<213> ORGANISM: Artificial Sequence
<220> FEATURE:
<223> OTHER INFORMATION: chemically synthesized

<400> SEQUENCE: 28
ctgatgctga tgctgtagtc gattagctag                                        30

<210> SEQ ID NO 29
<211> LENGTH: 23
<212> TYPE: DNA
<213> ORGANISM: Artificial Sequence
<220> FEATURE:
<223> OTHER INFORMATION: chemically synthesized

<400> SEQUENCE: 29
gtatgtgcga tgtcgtagct gta                                               23

<210> SEQ ID NO 30
<211> LENGTH: 15
<212> TYPE: DNA
<213> ORGANISM: Artificial Sequence
<220> FEATURE:
<223> OTHER INFORMATION: chemically synthesized

<400> SEQUENCE: 30
tgatgtcgta gcagt                                                        15
```